United States Patent
Loring et al.

(10) Patent No.: US 6,524,819 B1
(45) Date of Patent: Feb. 25, 2003

(54) DOWN SYNDROME CRITICAL REGION 1-LIKE PROTEINS

(75) Inventors: Jeanne F. Loring, Foster City, CA (US); Debora W. Tingley, San Francisco, CA (US); Carla M. Edwards, Half Moon Bay, CA (US); David G. Streeter, Boulder Creek, CA (US)

(73) Assignee: Incyte Genomics, Inc., Palo Alto, CA (US)

(*) Notice: Subject to any disclaimer, the term of this patent is extended or adjusted under 35 U.S.C. 154(b) by 10 days.

(21) Appl. No.: 09/614,474

(22) Filed: Jul. 11, 2000

(51) Int. Cl.[7] ............................ C12P 21/06; C12N 1/20; C12N 15/63; C12Q 1/68; G01N 33/53

(52) U.S. Cl. ................ 435/69.1; 435/252.3; 435/320.1; 435/6; 435/7.1; 536/23.1

(58) Field of Search ..................... 536/23.1; 435/69.1, 435/320.1, 252.3, 7.1, 5, 6; 530/300, 350

(56) References Cited

PUBLICATIONS

Minoshima, S. et al., "Metabolic Reduction in the Posterior Cingulate Cortex in Very Early Alzheimer's Disease", *Annals of Neurology*, 42:85–94 (1997).

Strittmatter, W.J. et al., "Apolipoprotein E: High–avidity binding to β–amyloid and increased frequency of type 4 allele in late–onset familial Alzheimer disease", *Proc. Natl. Acad. Sci..*, 90:1977–1981 (1993).

Selkoe, D.J., "Translating cell biology into therapeutic advances in Alzheimer's disease", *Nature*, 399:A23–A31 (1999).

Miyazaki, T. et al., "Molecular Cloning of a Novel Thyroid Hormone–responsive Gene, ZAKI–4, in Human Skin Fibroblasts", *J. Biol. Chem.*, 271:14567–14571 (1996).

Fuentes, J.J. et al., "A new human gene from the Down syndrome critical region encodes a proline–rich protein highly expressed in fetal brain and heart", *Hum. Mol. Genet.*, 4:1935–1944 (1995).

Strippoli, P. et al., "A New Gene Family Including DSCR1 (Down Syndrome Candidate Region 1) and ZAKI–4: Characterization from Yeast to Human and Identification of DSCR1–like 2, a Novel Human Member (DSCR1L2)", *Genomics*, 64:252–263 (2000).

Sutherland, M.K. et al., "Reduction of Thyroid Hormone Receptor c–ERB AαmRNA Levels in the Hippocampus of Alzheimer as Compared to Huntington Brain", *Neurobiol. Aging*, 13:301–312 (1992).

Belandia, B. et al., "Thyroid Hormone Negatively Regulates Transcriptional Activity of the the β–Armyloid Precursor Protein Gene", *J. Biol. Chem.*, 273:30366–30371 (1998).

Mayazaki, T., (Direct Submission) NCBI Accession No. BAA11911 (GI 1435040), Feb. 6, 1999.

Strippoli et al., (Direct Submission) NCBI Accession No. AAF01684 (GI 6017919), Apr. 20, 2000.

*Primary Examiner*—Gary Kunz
*Assistant Examiner*—Sharon Turner
(74) *Attorney, Agent, or Firm*—Incyte Genomics, Inc.

(57) ABSTRACT

The invention provides a mammalian nucleic acid molecule and fragments thereof. It also provides for the use of the mammalian nucleic acid molecule for the characterization, diagnosis, evaluation, treatment, of conditions, diseases and disorders associated with gene expression and for the production of a model system. The invention additionally provides expression vectors and host cells for the production of the protein encoded by the mammalian nucleic acid molecule.

13 Claims, 5 Drawing Sheets

|       |     |     |     |     | 190 |     |     | 199 |     | 208 |     | 217 |
|-------|-----|-----|-----|-----|-----|-----|-----|-----|-----|-----|-----|-----|
| 5'    |     |     |     |     | ATG | TCA | ACT | TTG | GAA | AAA | AAC | GTA | GTG | TNG |
|       |     |     |     |     |  M  |  S  |  T  |  L  |  E  |  K  |  N  |  V  |  V  |  X  |

| 226 |     | 235 |     |     |     | 244 |     | 253 |     | 262 |     | 271 |
| AGG | GGA | TCA | TAC | TTC | ATC | GGA | ATG | AGG | AGC | CCA | GGG | CAG | CAG | GGA |
|  R  |  G  |  S  |  Y  |  F  |  I  |  G  |  M  |  R  |  S  |  P  |  G  |  Q  |  Q  |  G  |

GGA ATG
 G   M

| 280 |     | 289 |     |     |     | 298 |     | 307 |     | 316 |     | 325 |
| CCT | GAA | GGA | GAT | CTT | GGA | TTC | TTA | TGC | TGC | ATA | GAC | AGG | GAC | TGG |
|  P  |  E  |  G  |  D  |  L  |  G  |  F  |  L  |  C  |  C  |  I  |  D  |  R  |  D  |  W  |

CAC GTC
 H   V

| 334 |     | 343 |     |     |     | 352 |     | 361 |     | 370 |     | 379 |
| ACT | CGT | TGT | TTT | GCA | GAA | GCC | TTT | CAA | GCA | ATC | ACT | GAC | TTC | AAT |
|  T  |  R  |  C  |  F  |  A  |  E  |  A  |  F  |  Q  |  A  |  I  |  T  |  D  |  F  |  N  |

GCT GTC
 A   V

| 388 |     | 397 |     |     |     | 406 |     | 415 |     | 424 |     | 433 |
| CCC | AAC | TCG | TTG | TTT | GCG | TGC | AAT | GTT | CAC | CAG | TCA | GTG | TTT | GAA | GGA |
|  P  |  N  |  S  |  L  |  F  |  A  |  C  |  N  |  V  |  H  |  Q  |  S  |  V  |  F  |  E  |  G  |

GAC CTC
 D   L

| 442 |     | 451 |     |     |     | 460 |     | 469 |     | 478 |     | 487 |
| AGC | AAG | GAA | AAA | TTT | GAG | GGA | CTG | TTT | CGG | ACT | TAT | GAT | GAC | TGT | GTG |
|  S  |  K  |  E  |  K  |  F  |  E  |  G  |  L  |  F  |  R  |  T  |  Y  |  D  |  D  |  C  |  V  |

GAA GAG
 E   E

FIGURE 1A

```
ACG TTC CAG CTA TTT AAG AGT TTC AGA CGT GTC ATA AAC TTC AGC AAT CCT
 T   F   Q   L   F   K   S   F   R   R   V   I   N   F   S   N   P
496                 505             514             523         532         541

AAA TCT GCA GCC CGA GCT AGG ATA GAG CTT CAT GAA ACC CAA TTC AGA GGG AAA
 K   S   A   A   R   A   R   I   E   L   H   E   T   Q   F   R   G   K
550                 559             568             577         586         595

AAA TTA AAG CTC TAC TTT GCA CAG ACT CAG GTT CCA GAG ACA GAT GGA GAC AAA
 K   L   K   L   Y   F   A   Q   T   Q   V   P   E   T   D   G   D   K
604                 613             622             631         640         649

CTG CAC TTG GCT CCA CCC CAG CCT AAA CAG GCC ATC AAC GAT TCG CCC CCT TCC
 L   H   L   A   P   P   Q   P   K   Q   A   I   N   D   S   P   P   S
658                 667             676             685         694         703

TCC CCA CCT GTT GGC TGG CAG CCC ATC AAC GAT GCC ACG CCA GTC CTC AAC TAT
 S   P   P   V   G   W   Q   P   I   N   D   A   T   P   V   L   N   Y
712                 721             730             739         748         757

GAC CTC TAT GCT GTG GCC AAA CTA GGA CCA GGA GAG AAG TAT GAG CTC CAT
 D   L   Y   A   V   A   K   L   G   P   G   E   K   Y   E   L   H
766                 775             784             793         802         811

FIGURE 1B
```

```
          820         829         838         847         856         865
GCA GGG ACT GAG TCC ACC CCA AGT GTC GTG CAC GTG TGC GAC AGT GAC ATA
 A   G   T   E   S   T   P   S   V   V   H   V   C   D   S   D   I 874         883         892         901         910         919
GAG GAA GAG GAC CCA AAG ACT TCC CCA AAG ACT CCA AAA ATC ATC CAA ACT CGG
 E   E   E   D   P   K   T   S   P   K   P   K   I   I   Q   T   R 928         937         946
CGT CCT GGC CTG CCA CCC TCC GTG TCC AAC  3'
 R   P   G   L   P   P   S   V   S   N
```

FIGURE 1C

FIGURE 2A

```
  1  MSTLEKNNVVXGMRGESYFIGMRSPGQQGH   DSCR1L1α
  1  MD--------CDV----------------    g1435040
  1  M--------LRDT----MKSWNDSQSD--    g6017919

31  VPEDGGLFLLCCIDRDWAVTRCFAE--EAF   DSCR1L1α
  6  -----------------------------    g1435040
 16  ---------LCSTDQEEEEEMIFGENEDDL   g6017919

59  QAITDFNDLPNSLFACNVHQSVFEGEESKE   DSCR1L1α
  6  -------STLVACVVDVEVFTNQEVKE      g1435040
 37  DEMMDLSDLPTSLFACSVHEAVFEAREQKE   g6017919

89  KFEGLFRTYDDCVTFQLFKSFRRVRINFSN   DSCR1L1α
 26  KFGGLFRTYDDCVTFQLFKSFRRVRINFSN   g1435040
 67  REEALFTIYDDQVTFQLFKSFRRVRINFSK   g6017919

119  PKSAAARARIELHETQFRGKKLKLYFAQVQT  DSCR1L1α
 56  PKSAAARARIELHETQFRGKKLKLYFAQVQT  g1435040
 97  PEAAARARIELHETDFNGQKLKLYFAQVQM   g6017919
```

FIGURE 2A

|     |   |   |   |   |   |   |   |   |   |   |   |   |   |   |   |   |   |   |   |   |   |   |   |   |   |   |   |   |   |        |
|-----|---|---|---|---|---|---|---|---|---|---|---|---|---|---|---|---|---|---|---|---|---|---|---|---|---|---|---|---|---|--------|
| 149 | P | E | T | D | G | D | K | L | H | L | A | P | P | Q | P | A | K | Q | F | L | I | S | P | P | S | S | P | P | V | G | DSCR1L1α |
| 86  | P | E | T | D | G | D | K | L | H | L | A | P | P | Q | P | A | K | Q | F | L | I | S | P | P | S | S | P | P | V | S | gl435040 |
| 127 | S | G | E | V | R | D | K | S | Y | L | L | P | P | Q | P | V | K | Q | F | L | I | S | P | P | A | S | P | P | V | G | g6017919 |
| 179 | W | Q | P | I | N | D | A | T | P | V | L | N | Y | D | L | L | Y | A | V | A | K | L | G | P | G | E | K | Y | E | L |   | DSCR1L1α |
| 116 | W | Q | P | I | N | D | A | T | P | V | L | N | Y | D | L | L | Y | A | V | A | K | L | G | P | G | E | K | Y | E | L |   | gl435040 |
| 157 | W | K | Q | S | E | D | A | M | P | V | I | N | Y | D | L | L | C | A | V | S | K | L | G | P | G | E | K | Y | E | L |   | g6017919 |
| 209 | H | A | G | T | E | S | T | P | S | V | V | V | H | V | C | D | S | D | I | E | E | E | E | D | P | K | T | S | P | K |   | DSCR1L1α |
| 146 | H | A | G | T | E | S | T | P | S | V | V | V | H | V | C | D | S | D | I | E | E | E | E | D | P | K | T | S | P | K |   | gl435040 |
| 187 | H | A | G | T | E | S | T | P | S | V | V | V | H | V | C | E | S | E | T | E | E | E | E | E | T | K | - | N | P | K |   | g6017919 |
| 239 | P | K | I | I | Q | T | R | R | P | G | L | P | P | S | V | S | N |   |   |   |   |   |   |   |   |   |   |   |   |   |   | DSCR1L1α |
| 176 | P | K | I | I | Q | T | R | R | P | G | L | P | P | S | V | S | N |   |   |   |   |   |   |   |   |   |   |   |   |   |   | gl435040 |
| 216 | Q | K | I | A | Q | T | R | R | P | D | P | P | T | A | A | L | N | E | P | Q | T | F | D | C | A | L |   |   |   |   | g6017919 |

FIGURE 2B

DOWN SYNDROME CRITICAL REGION 1-LIKE PROTEINS

FIELD OF THE INVENTION

This invention relates to nucleic acid molecules and amino acid sequences of a new mammalian protein and to their use in the characterization, diagnosis, and treatment of conditions such as Alzheimer's disease, Down syndrome and other forms of dementia.

BACKGROUND OF THE INVENTION

Alzheimer's disease is a progressive neurodegenerative disorder that is characterized by the formation of senile plaques and neurofibrillary tangles containing amyloid beta peptide. These plaques are found in limbic and association cortices of the brain, including hippocampus, temporal cortices, cingulate cortex, amygdala, nucleus basalis and locus caeruleus. Early in Alzheimer's pathology, physiological changes are visible in the cingulate cortex (Minoshima et al. (1997) Annals of Neurology 42:85–94). In subjects with advanced Alzheimer's disease, accumulating plaques damage the neuronal architecture in limbic areas and eventually cripple the memory process.

Approximately twenty million people worldwide suffer with dementia that results from Alzheimer's disease. The disease can be early onset affecting individuals as young as 30 years of age, or it can be familial or sporadic. Familial Alzheimer's disease was once thought to be inherited strictly as an autosomal dominant trait; however, this view is changing as more genetic determinants are isolated. For example, some normal allelic variants of apolipoprotein E (ApoE), which is found in senile plaques, can either protect against or increase the risk of developing the disease (Strittmatter et al. (1993) Proc Natl Acad Sci 90:1977–1981).

Mutations in four genes are known to predispose an individual to Alzheimer's disease: ApoE, amyloid precursor protein (APP), presenilin-1, and presenilin-2 (Selkoe (1999) Nature 399:A23–A31). The e4 allele of the ApoE gene confers increased risk for late onset Alzheimer's disease. β-amyloid protein (Aβ) is the major component of senile plaques, and it is normally formed when β- and γ-secretases cleave APP. In Alzheimer's disease patients, large quantities of Aβ are generated and accumulate extracelluarly in these neuropathological plaques.

Associations between Alzheimer's disease and many other genes and proteins have been reported. Fetal Alzheimer antigen an synuclein a are found in brain plaques and tangles. Inheritance of some gene polymorphisms is also linked to increased risk of developing the disease. For example, a polymorphism in the gene encoding β2-macroglobulin, a protein that can act as a protease inhibitor, is associated with increased risk for developing a late-onset form of Alzheimer's disease.

Experiments using microarray technology have provided additional evidence for changes in expression of specific genes in tissues from subjects with Alzheimer's disease. One such gene, Down syndrome critical region 1-like 1 (Mazowiecki et al. (1996) J Biol Chem 271:14567–14571) also named DSCR1L1 (g1435040), was found to be down-regulated more than two-fold in Alzheimer's tissue. DSCR1L1 encodes a thyroid hormone responsive protein and is a member of a gene family that includes DSCR1 (g7657042) and DSCR1L2 (g6017918). The first member of the family cloned, DSCR1, was named based on its proximity to the Down syndrome region of chromosome 21, but the function of the encoded protein and its role in Down syndrome, if any, remains unclear. The defining motifs of this family of proteins include an N-terminal RNA-binding domain, which is similar to those found in many RNA-binding proteins and in some single-stranded DNA-binding proteins, and a central short, unique serine-proline motif that includes an ISPPXSPP box that may be a target for phosphorylation (Fuentes et al. (1995) Hum Mol Genet 4:1935–1944).

Based on general features of the amino acid sequences, these DSCR1 genes likely encode proteins involved in transcriptional regulation and signal transduction (Strippoli et al. (2000) Genomics 64:252–263). The three genes appear to be differentially expressed: DSCR1 is highly expressed in fetal brain and heart, DSCR1L1 is evident in heart, brain, liver and skeletal muscle, and DSCR1L2 is expressed in most tissues including blood.

There are several connections between Alzheimer's disease and Down syndrome, such as the appearance of enhanced β-amyloid deposits in middle-aged Down syndrome patients. The thyroid hormone responsive properties of DSCR1L1 may be relevant to the role for this gene in Alzheimer's disease and/or Down syndrome: both Alzheimer's and Down's patients have been shown to have disturbances in thyroid hormone metabolism including elevated antithyroglobulin antibodies and reduced levels of prealbumin in the cerebrospinal fluid of Alzheimer's patients and pronounced subclinical hypothyroidism in Down's patients who have clinical manifestations of Alzheimer's disease (Sutherland et al. (1992) Neurobiol Aging 13:301–312). Conversely, hypothyroid patients display some of the same neurologic symptoms seen in Alzheimer's patients and a history of thyroid dysfunction is considered to be a risk factor for developing Alzheimer's disease. One possible connection is the discovery that thyroid hormone negatively regulates the transcriptional activity of the APP gene (Belandia et al. (1998) J Biol Chem 273:30366–30371); overexpression of APP has been hypothesized to cause neuronal degeneration by a mechanism involving increased production of β-amyloid protein. The down-regulation of the thyroid responsive DSCR1L1 gene and possibly other DSCR1 genes in Alzheimer's patients also provides a link between Alzheimer's and thyroid hormone function.

The discovery of additional mammalian nucleic acid molecules encoding members of the DSCR1 protein family may be used for the diagnosis, prognosis or treatment of Alzheimer's disease, Down syndrome and other forms of dementia.

SUMMARY OF THE INVENTION

The invention is based on the discovery of a substantially purified mammalian nucleic acid molecule encoding mammalian DSCR1L1α protein, which satisfies a need in the art by providing compositions useful in the characterization, diagnosis, and treatment of conditions such as Alzheimer's disease, Down syndrome and other forms of dementia.

The invention provides an isolated mammalian cDNA or a fragment thereof encoding a mammalian protein or a portion thereof selected from the group consisting of an amino acid sequence of SEQ ID NO:2, a variant having at least 95% identity to the amino acid sequence of SEQ ID NO:2, and an antigenic epitope of SEQ ID NO:2. The invention also provides an isolated mammalian cDNA or the complement thereof selected from the group consisting of a nucleic acid sequence of SEQ ID NO:1, a variant having at least 85% identity to the nucleic acid sequence of SEQ ID NO:1, and a fragment of SEQ ID NO:1. The invention additionally provides a composition, a substrate, and a probe comprising the cDNA, or the complement of the cDNA, encoding DSCR1L1α. The invention further provides a vector containing the cDNA, a host cell containing the vector and a method for using the cDNA to make DSCR1L1α. The invention still further provides a transgenic cell line or organism comprising the vector containing the cDNA encoding DSCR1L1α. The invention additionally provides a mammalian fragment or the complement thereof selected from the group consisting of SEQ ID NOs:3–9. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose Alzheimer's disease, Down syndrome and other forms of dementia. In another aspect, the cDNA or a fragment or a complement thereof may comprise an element on an array.

The invention additionally provides a method for using a cDNA or a fragment or a complement thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from DNA molecules, RNA molecules, peptide nucleic acids, artificial chromosome constructions, peptides, transcription factors, repressions, and regulatory molecules.

The invention provides a purified mammalian protein or a portion thereof selected from the group consisting of an amino acid sequence of SEQ ID NO:2, a variant having 95% identity to the amino acid sequence of SEQ ID NO:2, an antigenic epitope of SEQ ID NO:2, an oligopeptide of SEQ ID NO:2, and a biologically active portion of SEQ ID NO:2. The invention also provides a composition comprising the purified protein or a portion thereof in conjunction with a pharmaceutical carrier. The invention still further provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with Alzheimer's disease, Down syndrome or other forms of dementia.

The invention provides a method of using a mammalian protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of Alzheimer's disease, Down syndrome and other forms of dementia. The invention also provides a method of using a mammalian protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which bind specifically to DSCR1L1α. The invention also provides a method of using an antibody to diagnose Alzheimer's disease, Down syndrome and other forms of dementia comprising combining the antibody comparing the quantity of bound antibody to known standards, thereby establishing the presence of the disease. The invention further provides a method of using an antibody to treat Alzheimer's disease, Down syndrome and other forms of dementia comprising administering to a patient in need of such treatment a pharmaceutical composition comprising the purified antibody.

The invention provides a method for inserting a marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:1, and 3–9, transfonning the vector into an embryonic stem cell, selecting a transformed embryonic stem, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLE

FIGS. 1A, 1B, and 1C show the region of the human nucleic acid molecule (SEQ ID NO:1) encoding the human amino acid sequence (SEQ ID NO:2). The alignment was produced using MACDNASIS PRO software (Hitachi Software Engineering, South San Francisco Calif.).

FIGS. 2A and 2B demonstrate the chemical and structural similarity among the human DSCR1L1α (SEQ ID NO:1), human DSCR1L1 (g1435040;SEQ ID NO:10), and human DCSR1L2 (g6017919;SEQ ID NO:11). The alignment was produced using the MEGALIGN program (DNASTAR, Madison Wis.).

Table 1 shows rat and monkey nucleic acid sequences which have homology with SEQ ID NO:1 and includes their nucleotide length, biological source, region of overlap with SEQ ID NO:1, and percent identity with SEQ ID NO:1.

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All patents and publications are incorporated herein by reference and are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions "Down syndrome critical region 1-like 1α (DSCR1L1α) protein" refers to a substantially purified protein obtained from any mammalian species, including bovine, canine, marine, opine, porcine, rodent, simian, and preferably the human species, and from any source, whether natural, synthetic, semi-synthetic, or recombinant.

"Array" refers to an ordered arrangement of at least two nucleic acid molecules on a substrate. At least one of the nucleic acid molecules represents a control or standard sequence, and the other, a nucleic acid molecule of diagnostic interest. The arrangement of from about two to about 40,000 nucleic acid molecules on the substrate assures that the size and signal intensity of each labeled hybridization complex formed between a nucleic acid molecule and a sample nucleic acid is individually distinguishable.

The "complement" of a nucleic acid molecule of the Sequence Listing refers to a nucleic acid molecule which is completely complementary over its full length and which will hybridize to the nucleic acid molecule or an mRNA under conditions of high stringency.

"nucleic acid molecule" refers to an isolated polynucleotide, nucleic acid molecule, or any fragment or complement thereof. It may have originated recombinantly or synthetically, be double-stranded or single-stranded, represent coding and/or nonmoving sequence, an exon with or without an intron from a gnomic DNA molecule.

The phrase "nucleic acid molecule encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Ecol. 36: 290–300; Altschul et al. (1990) J Mol Biol 215:403–410) which provides identity within the conserved region. Brenner et al. (1998; Proc Natl Acad Sci 95:6073–6078) who analyzed BLAST for its ability to identify structural homology by sequence identity found 30% identity is a reliable threshold for sequence alignments of at least 150 residues and 40% is a reasonable threshold for alignments of at least 70 residues (Brenner et al., page 6076, column 2).

"Derivative" refers to a nucleic acid molecule or a protein that has been subjected to a chemical modification. Derivatization of a nucleic acid molecule can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, unregulated or present, or decreased, down regulated or absent, gene expression as detected by the absence, presence, or at least two-fold changes in the amount of transcribed messenger RNA or translated protein in a sample.

"Disorder" refers to conditions, diseases or syndromes in which the nucleic acid molecules and DSCR1 proteins are differentially expressed.

"Fragment" refers to a chain of consecutive nucleoside from about 200 to about 700 base pairs in length. Fragments may be used in PCR or hybridization technologies to identify related nucleic acid molecules and in binding assays to screen for a ligand. Nucleic acids and their ligand identified in this manner are useful as therapeutics to regulate replication, transcription or translation.

A "hybridization complex" is formed between a nucleic acid molecule and a nucleic acid of a sample when the purine of one molecule hydrogen bond with the pyrimidine of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a nucleic acid molecule molecule or polynucleotide, or to an epitope or a protein. Such ligand stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleoside in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligand or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a nucleic acid molecule that hybridizes to at least one nucleic acid in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM. or PRINTS analysis or an antigenic epitope of the protein identified using Kate-Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; gnomic DNA, RNA, or nucleic acid molecule in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which nucleic acid molecule or proteins are bound and includes membranes, filters, chips, slides, wafers, fibers, magnetic or nonmagnetic beads, gels, capillaries or other tubing, plates, polymers, and micro particles with a variety of surface forms including wells, trenches, pins, channels and pores.

"Variant" refers to molecules that are recognized variations of a nucleic acid molecule or a protein encoded by the nucleic acid molecule. Splice variants may be determined by BLAST score, wherein the score is at least 100, and most preferably at least 400. Allelic variants have a high percent identity to the nucleic acid molecule and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid.

The Invention

The invention is based on the discovery of new mammalian nucleic acid molecules which encode the mammalian protein DSCR1L1α, and on the use of the nucleic acid molecule, or fragments thereof, and protein, or portions thereof, as compositions in the characterization, diagnosis, treatment, or of conditions such as Alzheimer's disease, Down syndrome and other forms of dementia.

In one embodiment, the invention encompasses a polypeptide comprising the amino acid sequence of SEQ ID NO:2 as shown in FIGS. 1A, 1B, and 1C. DSCR1L1α has a single-stranded nucleic acid-binding domain characterized by positively charged and aromatic amino acids from residue 129 to residue 199, which is similar to known RNA recognition motifs. In addition, DSCR1L1α contains the ISPPXSPP box characteristic of DSCR1 proteins from residue 169 to residue 176. As shown in FIGS. 2A and 2B, DSCR1L1α shares chemical and structural homology with human DSCR1L1 (g1435040; SEQ ID NO:10), and human DCSR1L2 (g6017919; SEQ ID NO:11). In particular, DSCR1L1α shares 90.3% identity with DSCR1L1 and 57.3% identity with DSCR1L2. All three proteins share the single-stranded nucleic acid-binding domain and the ISPPXSPP box. SEQ ID NO:1 differs from the gene encoding DSCR1L1 (g1435039; SEQ ID NO:12) and the gene encoding DSCR1L2 (g6017918; SEQ ID NO:13) in the 5' untranslated region, and is further distinguished from these and other genes encoding DSCR1 family proteins by the first 70 amino acids encoded by the open reading frame from about amino acid residue M1 to about amino acid residue S70 of SEQ ID NO:1. A probe from the region of SEQ ID NO:1 from about nucleotide 1 to about nucleotide 400 would be useful for identifying naturally occurring molecules encoding DSCR1L1α, allelic variants, or related molecules. An antigenic epitope from the region of DSCR1L1α from about amino acid residue M1 to about amino acid residue S70 would be useful for the production of antibodies to DSCR1L1α which would distinguish between DSCR1L1α and similar proteins.

Electronic northern analysis shows the expression of this sequence in various libraries, with the highest abundance in tissues from the nervous system, including tissues associated with schizophrenia, Huntington's disease, epilepsy, and amyotrophic lateral sclerosis. Consistent with its observed 2-fold downregulation on microarrays hybridized from subjects with diagnosed Alzheimer's disease (U.S. Ser. No. 09/534,846, filed May 5, 2000, hereby incorporated by reference), is the absence of DSCR1L1α expression in 7 of 8 libraries from subjects with Alzheimer's disease.

Table 1 shows nucleic acid fragments from rat and monkey and their sequence coverage and identity with SEQ ID NO:1. Columns 1 and 2 list the SEQ ID NO and Incyte sequence identifier, respectively, for each nucleic acid sequence. Column 3 lists the nucleotide length for each fragment, Column 4, the range of nucleotide residues in SEQ ID NO:1 over which each fragment shows identity with SEQ ID NO:1, Column 5 identifies the source of the organism, and Column 6 shows the percent sequence identity between each fragment and SEQ ID NO:1 over the nucleotide range set forth in column 4.

These nucleic acid molecules are particularly useful for producing transgenic cell lines or organisms which model human disorders and upon which potential therapeutic treatments for such disorders may be tested. Of particular note is the expression of SEQ ID NO:9 in cingulate cortex, an area that shows functional deficits early in the Alzheimer's disease process. This monkey nucleic acid molecule would be useful in a model system of Alzheimer's disease. The monkey nucleic acid molecule may also be used as a probe to search for homologous human DSCR1L1 gene family sequences that similarly have expression restricted to cingulate cortex.

Characterization and Use of the Invention cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequences were chemically and/or electronically assembled from fragments including Incyte clones and extension and/or shotgun sequences using computer programs such as Phrap (P. Green, University of Washington, Seattle Wash.), GELVIEW Fragment Assembly system (Genetics Computer Group, Madison Wis.), and AUTOASSEMBLER application (PE Biosystems, Foster City, Calif.).

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Rockville Md.). Preferably, sequence preparation is automated with machines such as the HYDRA microdispenser (Robbins Scientific, Sunnyvale Calif.), MICROLAB 2200 (Hamilton, Reno Nev.), and the DNA ENGINE thermal cycler (PTC200; MJ Research, Watertown Mass.). Machines used for sequencing include the ABI 3700, 377 or 373 DNA sequencing systems (PE Biosystems), the MEGABACE 1000 DNA sequencing system (APB), and the like. The sequences may be analyzed using a variety of algorithms which are well known in the art and described in Ausubel (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative regions flanking the nucleic acid molecules of interest. Prefinished sequences (incomplete assembled sequences) are inspected for identity using various algorithms or programs such as CONSED (Gordon (1998 Genome Res. 8:195–202) which are well known in the art. Contaminating sequences including vector or chimeric sequences or deleted sequences can be removed or restored, respectively, organizing the prefinished sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries (Life Technologies; Clontech, Palo Alto Calif., respectively) may be used to extend the nucleic acid sequence. For all PCR-based methods, primers may be designed using commercially available software, such as OLIGO 4.06 Primer Analysis software (National Biosciences, Plymouth Minn.) to be about 22 to 30 nucleotides in length, to have a GC content of about 50% or more, and to anneal to a target molecule at temperatures from about 55° C. to about 68° C. When extending a sequence to recover regulatory elements, it is preferable to use genomic, rather than cDNA libraries.

Use of the Mammalian Nucleic Acid Molecule

Hybridization

The mammalian nucleic acid molecule and fragments thereof can be used in hybridization technologies for various purposes. A probe may be designed or derived from unique regions such as the 5' regulatory region or from a conserved motif such as the N-terminal RNA-binding domain found in the DSCR1 protein family and used in protocols to identify naturally occurring molecules encoding the mammalian protein, allelic variants, or related molecules. The probe may be DNA or RNA, is usually single stranded and should have at least 50% sequence identity to any of the nucleic acid sequences. Hybridization probes may be produced using oligolabeling, nick translation, end-labeling, or PCR amplification in the presence of labeled nucleotide. A vector containing the nucleic acid molecule or a fragment thereof may be used to produce an mRNA probe in vitro by addition of an RNA polymerase and labeled nucleoside. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formalize allows the reaction to occur at a lower temperature. Hybridization can be performed at low stringency with buffers, such as 5×SSC with 1% sodium dodecyl sulfate (SDS) at 60° C., which permits the formation of a hybridization complex between nucleic acid sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid molecules are completely complementary. In some membrane-based hybridizations, permeably 35% or most preferably 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual,* Cold Spring Harbor Press, Plain view N.Y.

Microarrays may be prepared and analyzed using methods known in the art. Oligonucleotides may be used as either probes or targets in a microarray. The microarray can be used to monitor the expression level of large numbers of genes simultaneously and to-identify genetic variants, mutations, and single nucleotide polymorphism. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application WO95/35505; Heller et al. (1997) Proc Natl Acad Sci 94:2150–2155; and Heller et al. (1997) U.S. Pat. No. 5,605,662.)

Hybridization probes are also useful in mapping the naturally occurring gnomic sequence. The probes may be hybridized to: 1) a particular chromosome, 2) a specific region of a chromosome, 3) artificial chromosome constructions such as human artificial chromosomes (HACs), yeast artificial chromosomes (YACs), bacterial artificial chromosomes (BACs), bacterial P1 constructions, or single chromosomes or 5) cDNA libraries made from any of these sources.

Expression

A multitude of nucleic acid molecules encoding the mammalian DSCR1L1α protein may be cloned into a vector and used to express the protein, or portions thereof, in host cells. The nucleic acid sequences can be engineered by such methods as DNA shuffling (Stammer and Cramer (1996) U.S. Pat. No. 5,830,721) and site-directed mutagenesis to create new restriction sites, alter glycosylation patterns, change Codo preference to increase expression in a particular host, produce splice variants, extend half-life, and the like. The expression vector may contain transcriptional and transnational control elements (promoters, enchanters, specific initiation signals, and polyadenylated 3' sequence) from various sources which have been selected for their efficiency in a particular host. The vector, nucleic acid molecule, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmic DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Reus sarcoma virus enchanter or SV40 or EBV-based vectors may also be used for high-level protein expression.

Routine cloning, subcloning, and propagation of nucleic acid sequences can be achieved using the multi functional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, daddies sequencing, single strand rescue with helper phage, and creation of nested deletions in the cloned sequence.

For long term production of recombinant proteins, the vector can be stable transformed into cell lines along with a selectable or visible marker gene on the same or on a separate vector. After transformation, cells are allowed to grow for about 1 to 2 days in enriched media and then are transferred to selective media. Selectable markers, indomitability, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, lucifers and the like, may be propagated using culture techniques. Visible markers are also used to quantify the amount of protein expressed by the introduced genes. Verification that the host cell contains the desired mammalian nucleic acid molecule is based on DNA-DNA or DNA-RNA hybridizations or PCR amplification techniques.

The host cell may be chosen for its ability to modify a recombinant protein in a desired fashion. Such modifications include acetylating, carboxylating, glycosylation, phosphorylation, limitation, acylation and the like. Post-transnational processing which cleaves a "prepro." form may also be used to specify protein targeting, folding, and/or activity. Different host cells available from the ATCC. (Manassas, Va.) which have specific cellular machinery and characteristic mechanisms for post-transnational activities may be chosen to ensure the correct modification and processing of the recombinant protein.

Recovery of Proteins from Cell Culture

Heterologous moieties engineered into a vector for ease of purification include glutathione S-transferals (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methyl amine-derivative polyethylene glycol is attached to poly(styrene-co-divinyl benzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivatized amino acids, and washing with dichloromethane and/or N,N-dimethylfonmamide. The peptide is cleaved between the peptide carboxyl terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431A Peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties,* WH Freeman, New York N.Y.).

Preparation and Screening of Antibodies

Various hosts including goats, rabbits, rats, mice, humans, and others may be immunized by injection with mammalian DSCR1L1α protein or any portion thereof. Adjuvants such as Freud's, mineral gels, and surface active substances such as lysolecithin, plutonic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridum technique, the human B-cell hybridoma technique, and the EBV-hybridoma technique. (See, e.g., Kohler et al. (1975) Nature 256:495–497, Kozbor et al. (1985) J. Immunol Methods 81:31–42; Cote et al. (1983Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The mammalian DSCR1L1α protein or a portion thereof may be used in screening assays of phagemid or B-lymphocyte immunoglobulin libraries to identify antibodies having the desired specificity. Numerous protocols for competitive binding or immunizes using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols,* Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or APB kits for incorporation of a labeled nucleotide such as $^{32}$P-dCTP, Cy3-dCTP or Cy5-dCTP or amino acid such as $^{35}$S-methionine (APB). Nucleoside and amino acids may be directly labeled with a variety of substances including fluorescent, chemiluminescent, or chromogenic agents, and the like, by chemical conjugation to amines, thiols and other groups present in the molecules using reagents such as BIODIPY or FITC. (Molecular Probes, Eugene Oreg.).

Diagnostics

The nucleic acid molecules, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Conditions, diseases or disorders associated with differential expression include: Alzheimer's disease, dementia, Down syndrome, Huntington's disease and Pick's disease. The diagnostic assay may use hybridization or amplification technology to compare gene expression in a biological sample from a patient to standard samples in order to detect altered gene expression. Qualitative or quantitative methods for this comparison are well known in the art.

For example, the nucleic acid molecule or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered (higher or lower) in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology,* Wiley-Interscience, New York N.Y.; and Pound, supra.)

Therapeutics

Chemical and structural similarity, e.g., in the context of the RNA-binding domain and the conserved serine/proline motif, exist between regions of the SEQ ID NO:2 and other DSCR1 family proteins such as human DSCR1, human DSCR1L1 (g1435040), and human DSCR1L2 (g6017919). In addition, gene expression is closely associated with nervous system tissues and appears to play a role in Alzheimer's disease and Down syndrome. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, Alzheimer's disease, dementia, Down syndrome, Huntington's disease and Pick's disease.

In another embodiment, a pharmaceutical composition comprising a substantially purified mammalian protein in conjunction with a pharmaceutical carrier may be administered to a subject to treat or prevent a condition associated with altered expression or activity of the endogenous protein including, but not limited to, those provided above.

In a further embodiment, a ligand which modulates the activity of the mammalian protein may be administered to a subject to treat or prevent a condition associated with altered linesman, expression, or activity of the protein including, but not limited to, those listed above. In one aspect, an antibody which specifically binds the mammalian protein may be used as a targeting or delivery mechanism for bringing a pharmaceutical agent to cells or tissue which express the mammalian protein.

In an additional embodiment, a vector capable of expressing the mammalian protein or a portion or derivative thereof may be administered to a subject to treat or prevent a condition associated with altered linesman, expression, or activity of protein including, but-not limited to, those described above.

In a still further embodiment, a vector expressing the complement of the nucleic acid molecule or fragments thereof may be administered to a subject to treat or prevent a condition associated with altered linesman, expression, or activity of the protein including, but not limited to, those described above.

Any of the nucleic acid molecules, complementary molecules and fragments thereof, proteins or portions thereof, vectors delivering these nucleic acid molecules or proteins, and their ligand may be administered in combination with other therapeutic agents. Selection of the agents for use in combination therapy may be made by one of ordinary skill in the art according to conventional pharmaceutical principles. A combination of therapeutic agents may act synergistically to effect treatment of a particular condition at a lower dosage of each agent.

Modification of Gene Expression Using Nucleic Acids

Gene expression may be modified by designing complementary or antigens molecules (DNA, RNA, or PNA) to the control, 5', 3', or other regulatory regions of the mammalian gene. Oligonucleotides designed with reference to the transcription initiation site are preferred. Similarly, inhibition can be achieved using triple helix base-pairing which inhibits the binding of polymerase, transcription factors, or regulatory molecules (Gee et al. In: Huber and Carr (1994) *Molecular and Immunologic Approaches,* Futura Publishing, Mt. Kisco N.Y., pp. 163–177). A complementary molecule may also be designed to block translation by preventing binding between ribosomes and mRNA. In one alternative, a library of nucleic acid molecules or fragments thereof may be screened to identify those which specifically bind a regulatory, nontranslated sequence.

Ribosomes, enzymatic RNA molecules, may also be used to catalyze the specific cleavage of RNA. The mechanism of ribosome action involves sequence-specific hybridization of the ribosome molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribosomes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening Assays

The nucleic acid molecule encoding the mammalian protein may be used to screen a library of molecules for specific binding affinity. The libraries may be DNA molecules, RNA molecules, PNAs, peptides, proteins such as transcription factors, enchanters, repressions, and other ligand which regulate the activity, replication, transcription, or translation of the nucleic acid molecule in the biological system. The assay involves combining the mammalian nucleic acid molecule or a fragment thereof with the library of molecules under conditions allowing specific binding, and detecting specific binding to identify at least one molecule which specifically binds the nucleic acid molecule.

Similarly the mammalian protein or a portion thereof may be used to screen libraries of molecules in any of a variety of screening assays. The portion of the protein employed in such screening may be free in solution, affixed to an biotic or biotic substrate (e.g. borne on a cell surface), or located intra cellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs, or any other ligand, which specifically binds the protein. One method for high throughput screening using very small assay volumes and very small amounts of test compound is described in U.S. Pat. No. 5,876,946, which screens large numbers of molecules for enzyme inhibition or receptor binding.

Purification of Ligand

The nucleic acid molecule or a fragment thereof may be used to purify a ligand from a sample. A method for using a mammalian nucleic acid molecule or a fragment thereof to purify a ligand would involve combining the nucleic acid molecule or a fragment thereof with a sample under conditions to allow specific binding, detecting specific binding, recovering the bound protein, and using an appropriate agent to separate the nucleic acid molecule from the purified ligand.

Similarly, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, hemostatic processes, and lethality are used to generate a toxicity profile and to assess the consequences on human health following exposure to the agent.

Genetic toxicology identifies and analyzes the ability of an agent to produce genetic mutations Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle which produces the number of organisms needed to satisfy statistical requirements.

Acute toxicity tests are based on a single administration of the agent to the subject to determine the symptom ology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. Nos. 4,736,866; 5,175,383; and 5,767,337). In some cases, the introduced gene may be activated at a specific time in a specific tissue type during fetal development or postnatal. Expression of the transcend is monitored by analysis of phenotype or tissue-specific mRNA expression, in transgenic animals before, during, and after being challenged with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knocking rodent strains. Mouse ES cells, such as the mouse 129/SvJ cell line, are derived from the early mouse embryo and are grown under culture conditions well known in the art. Vectors for knockout strains contain a disease gene candidate modified to include a marker gene which disrupts transcription and/or translation in vivo. The vector is introduced into ES cells by transformation methods such as electroporation, lappaceum delivery, micro injection, and the like which are well known in the art. The endogenous rodent gene is replaced by the disrupted disease gene through homologous recombination and integration during cell division. Then transformed ES cells are selected under conditions, identified, and preferably micro injected into mouse cell blastocyst such as those from the C57BL/6 mouse strain. The blastocyst are surgically transferred to pseudo pregnant dams and the resulting chimeric progeny are genotype and bred to produce heterozygous or homozygous strains.

ES cells are also used to study the differentiation of various cell types and tissues in vitro, such as neural cells, hematopoietic lineages, and cardiomyocytes (Bain et al. (1995) Dev Biol 168:342–357; Wiles and Keeler (1991) Development 111 :259–267; and Klug et al. (1996) J Clin Invest 98:216–224). Recent developments demonstrate that ES cells derived from human blastocyst may also be manipulated in vitro to differentiate into eight separate cell lineages, including endoderm, mesoderm, and ectodermal cell types (Thomson (1998) Science 282:1145–1147).

Knockout Analysis

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudo pregnant dams. Transgenic progeny are crossbred to obtain homozygous inbred lines.

Knockin Analysis

Totipotent ES cells, present in the early stages of embryonic development, can be used to create knocking humanized animals (pigs) or transgenic animal models (mice or rats) of human diseases. With knocking technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc Natl Acad Sci 95:11371–11376; Baudoin et al. (1998) Genes Dev 12:1202–1216; and Zhuang et al. (1998) Mol Cell Biol 18:3340–3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human-surrogates in vaccine and drug evaluations, and their responses are relevant to human exposures under similar conditions. Cynomolgus monkeys (*Macaca fascicularis, Macaca mulatta*) and common marmosets (*Callithrix iacchus*) are the most common non-human primates (NHPS) used in these investigations. Since great cost is associated with developing and maintaining a colony of NHPS, early research and toxicological studies are usually carried out in rodent models. In studies using behavioral measures such as drug addiction, NHPS are the first choice test animal. In addition, NHPS and individual humans exhibit differential sensitivities to many drugs and toxins and can be classified as "extensive metabolites" and "poor metabolites" of these agents.

In additional embodiments, the nucleic acid molecules which encode the mammalian protein may be used in any molecular biology techniques that have yet to be developed, provided the new techniques rely on properties of nucleic acid molecules that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, the preparation of the human hippocampal cDNA library, HIPONON02, is described.

I cDNA Library Construction

The human hippocampal cDNA library, HIPONON02, was constructed from tissue obtained from the hippocampus of a 72-year-old Caucasian female, who died from an intracranial hemorrhage. The frozen tissue was homogenized and lysed in TRIZOL reagent (1 g tissue/10 ml; Life Technologies), using a POLYTRON homogenizer (PT-3000; Brinkmann Instruments Westbury N.Y.). Following homogenization, chloroform was added (1:5 v/v chloroform:homogenate), and the lysate was centrifuged. The aqueous layer was removed, and the RNA was precipitated with isopropanol. The RNA was resuspended in DEPC-treated water and digested with DNase I (Life Technologies) for 25 min at 37° C. The RNA was re-extracted with acid phenol-chloroform, pH 4.7, and precipitated using 0.3M sodium acetate and 2.5 volumes ethanol.

Messenger RNA (mRNA) was isolated using the OLIGOTEX kit (Qiagen, Valencia Calif.) and used to construct the cDNA library. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors, and digested with NotI (New England Biolabs, Beverly Mass.). The cDNAs were fractionated on a SEPHAROSE CL-2B column (APB), and those cDNAs exceeding 800 bp were ligated into the NotI and EcoRI sites of the PSPORT1 plasmid (Life Technologies). The plasmid was transformed into competent DH5a cells (Life Technologies) or ELECTROMAX DH10B cells (Life Technologies).

II Normalization of cDNA Libraries

For purposes of example, the normalization of a human brain library is described. About $1.13 \times 10^6$ independent clones of the HIPONOT01 plasmid library in *E. coli* strain DH12S competent cells (Life Technologies) were grown in liquid culture under carbenicillin (25 mg/l) and methicillin (1 mg/ml) selection following transformation by electroporation. To reduce the number of excess cDNA copies according to their abundance levels in the library, the cDNA library was then normalized in a single round according to the procedure of Soares et al. (1994, Proc Natl Acad Sci 91:9228–9232), with the following modifications. The primer to template ratio in the primer extension reaction was increased from 2:1 to 10:1. The ddNTP concentration in the reaction was reduced to 150 $\mu$M for each ddNTP to allow the generation of longer (400–1000 bases) primer extension products. The reannealing hybridization was extended from 13 to 48 hr. The single stranded DNA circles of the normalized library were purified by hydroxyapatite chromatography and converted to partially double-stranded by random priming, followed by electroporation into *E. coli* strain DH10B competent cells (Life Technologies).

III Construction of pINCY Plasmid

The plasmid was constructed by digesting the pSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, *E. coli* strain JM109.

An intermediate plasmid produced by the bacteria (pSPORT 1-ΔRI) showed no digestion with EcoRI and was digested with Hind III (New England Biolabs) and the overhanging ends were again filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

IV Isolation and Sequencing of cDNA Clones

Plasmid DNA was released from the cells and purified using either the MINIPREP kit (Edge Biosystems, Gaithersburg Md.) or the REAL PREP 96 plasmid kit (Qiagen). This kit consists of a 96-well block with reagents for 960 purifications. The recommended protocol was employed except for the following changes: 1) the bacteria were cultured in 1 ml of sterile TERRIFIC BROTH (BD Biosciences) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

The cDNAs were prepared for sequencing using the MICROLAB 2200 system (Hamilton,) in combination with the DNA ENGINE thermal cyclers (MJ Research). The cDNAs were sequenced by the method of Sanger and Coulson (1975; J Mol Biol 94:441–448) using an ABI PRISM 377 sequencing system (PE Biosystems) or the MEGABACE 1000 DNA sequencing system (APB). Most of the isolates were sequenced according to standard ABI protocols and kits (PE Biosystems) with solution volumes of 0.25×–1.0×concentrations. In the alternative, cDNAs were sequenced using solutions and dyes from APB.

V Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using OLIGO 4.06 software (National Biosciences), to be about 22 to 30 nucleotides in length, to have a GC content of about 50% or more, and to anneal to the target sequence at temperatures of about 68 C. to about 72 C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C., three min; Step 2: 94 C., 15 sec; Step 3: 60 C., one min; Step 4: 68 C., two min; Step 5: Steps 2, 3, and 4 repeated 20 times; Step 6: 68 C., five min; Step 7: storage at 4C. In the alternative, the parameters for primer pair T7 and SK+ (Stratagene) were as follows: Step 1: 94 C., three min; Step 2: 94 C., 15 sec; Step 3: 57 C., one min; Step 4: 68 C., two min; Step 5: Steps 2, 3, and 4 repeated 20 times; Step 6: 68 C., five min; Step 7: storage at 4 C.

The concentration of DNA in each well was determined by dispensing 100 μl PICOGREEN quantitation reagent (0.25% reagent in 1×TE, v/v; Molecular Probes) and 0.5 μl of undiluted PCR product into each well of an opaque fluorimeter plate (Corning, Acton Mass.) and allowing the DNA to bind to the reagent. The plate was scanned in a Fluoroskan II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC 18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37 C. in 384-well plates in LB12×carbenicillin liquid media.

The cells were lysed, and DNA was amplified using primers, Taq DNA polymerase (APB) and Pfu DNA polymerase (Stratagene) with the following parameters: Step 1: 94 C., three min; Step 2: 94 C., 15 sec; Step 3: 60 C., one min; Step 4: 72 C., two min; Step 5: steps 2, 3, and 4 repeated 29 times; Step 6: 72 C. five min; Step 7: storage at 4 C. DNA was quantified using PICOGREEN quantitative reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (PE Biosystems).

VI Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda Md.; http://www.ncbi.nlm.nih.gov/gorf/bl2.html), includes various sequence analysis programs including "blastn" that is used to align nucleic acid molecules and BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: –2; Open Gap: 5 and Extension Gap: 2 penalties; Gap×dropoff: 50; Expect: 10; Word Size: 11; and Filter: on. Identity is measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The mammalian cDNAs of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/EXON MAPPER algorithms that analyze the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1 \times 10^{-8}$. The templates were also subjected to frameshift FASTx against GENPEPT, and homolog match was defined as having an E-value of $\leq 1 \times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. Nos. 08/812,290 and 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://Hpfam.wustl.edu/).

The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VII Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNA encoding DSCR1L1α that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C. for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 $\mu$g. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110 C. oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C.; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 $\mu$l TE buffer, denaturing by heating to 100 C. for five min, and briefly centrifuging. The denatured cDNA is then added to a REDIPRIME tube (APB), gently mixed until blue color is evenly distributed, and briefly centrifuged. Five $\mu$l of [$^{32}$P]dCTP is added to the tube, and the contents are incubated at 37 C. for 10 min. The labeling reaction is stopped by adding 5 $\mu$l of 0.2M EDTA, and probe is purified from unincorporated nucleotides using a PROBEQUANT G-50 microcolumn (APB). The purified probe is heated to 100 C. for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 μl TE buffer and adding 5 μl 5×buffer, 1 μl 0.1 M DTT, 3 μl Cy3 or Cy5 labeling mix, 1 μl RNase inhibitor, 1 μl reverse transcriptase, and 5 μl xyeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample MRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C. for two hr. The reaction mixture is then incubated for 20 min at 85 C., and probes are purified using two successive CHROMA SPIN+TE 30 columns (Clontech, Palo Alto Calif.). Purified probe is ethanol precipitated by diluting probe to 90 μl in DEPC-treated water, adding 2 μl 1 mg/ml glycogen, 60 μl 5 M sodium acetate, and 300 μl 100% ethanol. The probe is centrifuged for 20 min at 20,800×g, and the pellet is resuspended in 12 μl resuspension buffer, heated to 65 C. for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1× high phosphate buffer (0.5 M NaCl, 0.1 M $Na_2HPO_4$, 5 mM EDTA, pH 7) at 55 C. for two hr. The probe, diluted in 15 ml fresh hybridization solution, is then added to the membrane. The membrane is hybridized with the probe at 55 C. for 16 hr. Following hybridization, the membrane is washed for 15 min at 25 C. in 1 mM Tris (pH 8.0), 1% Sarkosyl, and four times for 15 min each at 25 in 1 mM Tris (pH 8.0) To detect hybridization complexes, XOMAT-AR film (Eastman Kodak, Rochester N.Y.) is exposed to the membrane overnight at −70 C., developed, and examined visually.

Polymer Coated Slide-based Hybridization

Probe is heated to 65 C. for five min, centrifuged five min at 9400 rpm in a 5415 C. microcentrifuge (Eppendorf Scientific, Westbury N.Y.), and then 18 μl is aliquoted onto the array surface and covered with a coverslip. The arrays are transferred to a waterproof chamber having a cavity just slightly larger than a microscope slide. The chamber is kept at 100% humidity internally by the addition of 140 μl of 5×SSC in a corner of the chamber. The chamber containing the arrays is incubated for about 6.5 hr at 60 C. The arrays are washed for 10 min at 45 C. in 1×SSC, 0.1% SDS, and three times for 10 min each at 45 C. in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe MRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20× microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Electronic Analysis

BLAST was used to search for identical or related molecules in the GenBank or LIFESEQ databases (Incyte Genomics). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

Electronic northern analysis was performed at a product score of 70. All sequences and cDNA libraries in the LWFESEQ database were categorized by system, organ/tissue and cell type. The categories included cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. In a non-normalized library, expression levels of two or more are significant.

IX Complementary Molecules

Molecules complementary to the cDNA, from about 5 (PNA) to about 5000 bp (complement of a cDNA insert), are used to detect or inhibit gene expression. These molecules are selected using OLIGO 4.06 software (National Biosciences). Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the mammalian protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the mammalian protein.

Expression of DSCR1L1α

Expression and purification of the mammalian protein are achieved using either a mammalian cell expression system or an insect cell expression system. The pUB6/V5-His vector system (Invitrogen, Carlsbad Calif.) is used to express DSCR1L1α in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6xHis) sequence for rapid purification on PROBOND resin (Invitrogen). Transformed cells are selected on media containing blasticidin.

Spodoptera frugiperda (Sf9) insect cells are infected with recombinant *Autographica califomica* nuclear polyhedrosis virus (baculovirus). The polyhedrin gene is replaced with the mammalian cDNA by homologous recombination and the polyhedrin promoter drives cDNA transcription. The protein is synthesized as a fusion protein with 6xhis which enables purification as described above. Purified protein is used in the following activity and to make antibodies.

XI Production of Antibodies

DSCR1L1α is purified using polyacrylamide gel electrophoresis and used to immunize mice or rabbits. Antibodies are produced using the protocols below. Alternatively, the amino acid sequence of DSCR1L1α is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an ABI 431A peptide synthesizer (PE Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XIV Two-Hybrid Screen

A yeast two-hybrid system, MATCHMAKER LexA Two-Hybrid system (Clontech Laboratories, Palo Alto Calif.), is used to screen for peptides that bind the mammalian protein of the invention. A cDNA encoding the protein is inserted into the multiple cloning site of a pLexA vector, ligated, and transformed into *E. coli*. cDNA, prepared from mRNA, is inserted into the multiple cloning site of a pB42AD vector, ligated, and transformed into *E. coli* to construct a cDNA library. The pLexA plasmid and pB42AD-cDNA library constructs are isolated from *E. coli* and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30 C. until the colonies have grown up and are counted. The colonies are pooled in a minimal volume of 1×TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C. until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the mammalian protein, is isolated from the yeast cells and characterized.

XIV Demonstration of Protein Activity

DSCR1L1α, or biologically active fragments thereof, are labeled with $^{125}$I Bolton-Hunter reagent (Bolton et al. (1973) Biochem J 133:529–539). Candidate ligand molecules previously arrayed in the wells of a multi-well plate are incubated with the labeled DSCR1L1α, washed, and any wells with labeled DSCR1L1α complex are assayed. Data obtained using different concentrations of DSCR1L1α are used to calculate values for the number, affinity, and association of DSCR1L1α with the candidate ligand molecules.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

TABLE 1

| Nucleic Acid SEQ ID NO: | Incyte Sequence Identifier | Nucleotide Length | Organism | Overlap with SEQ ID NO:1 | % Identity with SEQ ID NO:1 |
| --- | --- | --- | --- | --- | --- |
| 3 | 219435.1 | 1021 | Rat | 443–954 | 86 |
|  |  |  |  | 1040–1212 | 87 |
| 4 | 271176.1 | 193 | Rat | 1323–1461 | 91 |
| 5 | 291862.1 | 1348 | Rat | 2419–2517 | 94 |
|  |  |  |  | 2158–2299 | 86 |
| 6 | 299263.1 | 531 | Rat | 668–794 | 86 |
|  |  |  |  | 884–954 | 89 |
| 7 | 219652.1 | 233 | Rat | 1683–1765 | 89 |
|  |  |  |  | 1593–1644 | 90 |
| 8 | 206751.1 | 615 | Rat | 734–837 | 82 |
| 9 | 702110167H1 | 297 | Monkey | 218–274 | 94 |

What is claimed is:

1. An isolated nucleic acid molecule comprising a polynucleotide having the nucleic acid sequence of SEQ ID NO:1 or the complement of SEQ ID NO:1.

2. A composition comprising the nucleic acid molecule or the complement of the nucleic acid molecule of claim 1.

3. A substrate comprising the nucleic acid molecule or the complement of the nucleic acid molecule of claim 1.

4. A probe comprising nucleotide 1 to nucleotide 400 of SEQ ID NO:1 or the complement of nucleotide 1 to nucleotide 400 of SEQ ID NO:1.

5. A vector comprising the nucleic acid molecule of claim 1.

6. A host cell comprising the vector of claim 5.

7. A method for producing a protein, the method comprising:
   a) culturing the host cell of claim 6 under conditions for protein expression; and
   b) recovering the protein from the host cell culture.

8. A transgenic cell line or organism comprising the vector of claim 5.

9. A method for detecting differential expression of a nucleic acid molecule in a sample containing nucleic acid comprising:
   a) hybridizing the nucleic acid molecule of claim 2 to nucleic acids in the sample, thereby forming hybridization complexes; and
   b) comparing the hybridization complexes with standards, wherein the comparison indicates the presence of differential expression of the nucleic acid molecule in the sample.

10. The method of claim 9 further comprising amplifying the nucleic acids of the sample prior to hybridization.

11. The method of claim 9 wherein decreased expression of the nucleic acid molecule of claim 2 is diagnostic of Alzheimer's disease.

12. A method of using a nucleic acid molecule to screen a plurality of molecules or compounds, the method comprising:
   a) combining the nucleic acid molecule of claim 1 with a plurality of molecules or compounds under conditions to allow specific binding; and
   b) detecting specific binding, thereby identifying a molecule or compound which specifically binds the nucleic acid molecule.

13. The method of claim 12 wherein the molecules or compounds are selected from DNA molecules, RNA molecules, peptide nucleic acids, artificial chromosome constructions, peptides, transcription factors, repressor, and regulatory molecules.

* * * * *

Disclaimer 6,524,819 B1—Jeanne F. Loring, Foster City, CA (US); Debora W. Tingley, San Francisco, CA (US); Carla M. Edwards, Half Moon Bay, CA (US); David G. Streeter, Boulder Creek, CA (US). DOWN SYNDROME CRITICAL REGION 1-LIKE PROTEINS. Patent dated Feb. 25, 2003. Disclaimer filed Jun. 24, 2004, by the assignee, Incyte Genomics, Inc.

Hereby enters this disclaimer to claim 8, of said patent.

*(Official Gazette, August 17, 2004)*

SEQUENCE LISTING

```
<160> NUMBER OF SEQ ID NOS:  13

<210> SEQ ID NO 1
<211> LENGTH: 3159
<212> TYPE: DNA
<213> ORGANISM: Homo sapiens
<220> FEATURE:
<221> NAME/KEY: misc_feature
<223> OTHER INFORMATION: Incyte ID No: 247500.5
<221> NAME/KEY: unsure
<222> LOCATION: 216, 3091, 3093, 3103
<223> OTHER INFORMATION: a, t, c, g, or other

<400> SEQUENCE: 1
ccagctatta gggagactcc agcccttgc caggcgagag agtggatggt caccctccat      60
ggaggaagtg tttcccaagg gtgtctgctg gggaaggaaa gcatgatgca gtgcagatta     120
atcagagaga agagccaacg tctcgtctac ctttttttgt tgaaaacaaa caaaacgtga     180
ttgtatgtca actttggaaa aaaacaacgt agtgtnggga atgaggggag aatcatactt     240
catcggaatg aggagcccag ggcagcaggg acacgtccct gaagatggag gacttttctt     300
actgtgctgc atagacaggg actgggctgt cactcgttgt tttgcagaag aagcctttca     360
agcaatcact gacttcaatg acctccccaa ctcgttgttt gcgtgcaatg ttcaccagtc     420
agtgtttgaa ggagaagaga gcaaggaaaa atttgaggga ctgtttcgga cttatgatga     480
ctgtgtgacg ttccagctat ttaagagttt cagacgtgtc cgtataaact tcagcaatcc     540
```

-continued

| | | | |
|---|---|---|---|
| taaatctgca gcccgagcta ggatagagct tcatgaaacc caattcagag ggaaaaaatt | 600 |
| aaagctctac tttgcacagg ttcagactcc agagacagat ggagacaaac tgcacttggc | 660 |
| tccaccccag cctgccaaac agtttctcat ctcgcccct tcctcccac ctgttggctg | 720 |
| gcagcccatc aacgatgcca cgccagtcct caactatgac ctcctctatg ctgtggccaa | 780 |
| actaggacca ggagagaagt atgagctcca tgcagggact gagtccaccc caagtgtcgt | 840 |
| cgtgcacgtg tgcgacagtg acatagagga agaagaggac ccaaagactt ccccaaagcc | 900 |
| aaaaatcatc caaactcggc gtcctggcct gccaccctcc gtgtccaact gagctgcctg | 960 |
| ctccttctcg ataatagccg tctcctcttt atcatgcttt ttccccctgt tgtttgtcaa | 1020 |
| aaaaaattgc ctttaaattc ctgggtgttt ggttgtttga gattccttcc ttgttatcaa | 1080 |
| gcctctcgga caaagggct aggaaaaggt gatatgtctc ctgatcatat catacccatt | 1140 |
| aagtataacc cattatttag aaggttctag ggaaaaaagt agtattttct tattaaacaa | 1200 |
| tcagcacagc ctatatcttt gttctctcat gttgatccaa gccagagaca tcagtaacaa | 1260 |
| atagcacctg tgttgtttgt gagctgtttc agtcccagtc ctgatgtgtg tgcgttgttc | 1320 |
| tctcctggcc acttaaatag gaccatatgt aaacttgact ttgactgcat gagatatccc | 1380 |
| tatctggtct cactcagtcc tctgcatccc aacattccca ggacatgcat gatcaccagc | 1440 |
| atttatttc attatttgag gatatcttat aactcacaga ttgtcagcat ccagccatgt | 1500 |
| cctatctaga ttaggaaaat gatcagaata ttccagctca caagtctgg gtatattcac | 1560 |
| tattgtgagt caatacacca tagctctgtt gaaattcctg gaggcaaaat tgaccttggc | 1620 |
| cccaaagata ttcctcaata gatttcaaac accactcccc tgtagaactc tcccagcctc | 1680 |
| gttggggagg cttgtccagg gtgatagaga ctgatttcag acaaacctat ttattacaaa | 1740 |
| agtttcatgg tgtctgaatg attgttttct ctctttgtat atttgtacaa atgtttcagc | 1800 |
| tgtgctttta aaaatctgg atgtttttta tttagtgatt gttcgacaat tagctgcttc | 1860 |
| aaaacataat gtgcattgct tatgaatgcc ttcatatact aatacagata ctctgataat | 1920 |
| attacactct aataaggata atgctgaatt ttgaaaggac acaaaacatc taatgccaat | 1980 |
| atatacatga ttagccaaca tctttgctat caagaccact tgttttaaa taaagatgca | 2040 |
| agtgtcagtt gtagattatt gggatgaagc taaatcccca gaatggcagc agcagctgag | 2100 |
| catgttaaaa tggggaagga tgatagctac atgtatgccg gtcctactca cgcgacaccc | 2160 |
| gtgtgctcaa aaaagttatt tgtttttgtt acgtgtgatt tttctatttc tctagcccaa | 2220 |
| agtgcattac agaagataca cctatagaac cattaccttc tgctatgtgt gccaggcctc | 2280 |
| atctactcct gtacattaat gaattacttt agatgcaaac gcagattaca atggagtggg | 2340 |
| gaagtacttt cattacccaa gcctcagaaa acacacaag aacaataaca cagcaaacag | 2400 |
| attgagggat tgttgtggtt tttgactaag gtgtatgtta gtttcatcag aaacttaaaa | 2460 |
| catagactga tcactcagaa attaaagtcc gttttactgt gaatatagca atatagtact | 2520 |
| ggacacagta ctggtgaaac tgaggagagc attgcttgta aaatcctgag tttccataag | 2580 |
| gaaaatgaaa actccttta aaaataaaat ctgaggagtg tacaataagc atatgctttg | 2640 |
| actttccttt gctgtggagg ttttggtttt tcattgatg ataaacgact acagactag | 2700 |
| tagtggagaa atggtgtcct ctagtggaag aaatagtagg ctccgctatt cagatgcaga | 2760 |
| gcactgcagc atccagcctt tcaaagctga ctcttctcaa tcatctgtgg gtcatttgac | 2820 |
| ttgattttt aagctaccct gaatttccag aatgcaggtt ctaaagaaat ctagatgaga | 2880 |
| gaaagtattt gaaaatgatt tttaaatgtt ttttaaaaga cacatctgac attttaaca | 2940 |

```
acttagtaaa agttgaaatg accattctgt gtagtcataa aagaaacaca atgaagtgta    3000
tggcctctgg agttagtctt agtaaaactt attgctctgt gtcaatgtta acctgtctca    3060
gatcaagtaa ttctttcact aggttgggtt ncngagggg ganaagaggg gctttcctag     3120
gagaacgata agaaatggaa agactccttg aagtgttgc                            3159
```

<210> SEQ ID NO 2
<211> LENGTH: 255
<212> TYPE: PRT
<213> ORGANISM: Homo sapiens
<220> FEATURE:
<221> NAME/KEY: misc_feature
<223> OTHER INFORMATION: Incyte ID No: 247500.5
<221> NAME/KEY: unsure
<222> LOCATION: 11
<223> OTHER INFORMATION: unknown or other

<400> SEQUENCE: 2

```
Met Ser Thr Leu Glu Lys Asn Asn Val Val Xaa Gly Met Arg Gly
  1               5                  10                  15

Glu Ser Tyr Phe Ile Gly Met Arg Ser Pro Gly Gln Gln Gly His
             20                  25                  30

Val Pro Glu Asp Gly Gly Leu Phe Leu Leu Cys Cys Ile Asp Arg
         35                  40                  45

Asp Trp Ala Val Thr Arg Cys Phe Ala Glu Glu Ala Phe Gln Ala
     50                  55                  60

Ile Thr Asp Phe Asn Asp Leu Pro Asn Ser Leu Phe Ala Cys Asn
 65                  70                  75

Val His Gln Ser Val Phe Glu Gly Glu Glu Ser Lys Glu Lys Phe
             80                  85                  90

Glu Gly Leu Phe Arg Thr Tyr Asp Asp Cys Val Thr Phe Gln Leu
         95                 100                 105

Phe Lys Ser Phe Arg Arg Val Arg Ile Asn Phe Ser Asn Pro Lys
        110                 115                 120

Ser Ala Ala Arg Ala Arg Ile Glu Leu His Glu Thr Gln Phe Arg
        125                 130                 135

Gly Lys Lys Leu Lys Leu Tyr Phe Ala Gln Val Gln Thr Pro Glu
        140                 145                 150

Thr Asp Gly Asp Lys Leu His Leu Ala Pro Pro Gln Pro Ala Lys
        155                 160                 165

Gln Phe Leu Ile Ser Pro Pro Ser Ser Pro Pro Val Gly Trp Gln
        170                 175                 180

Pro Ile Asn Asp Ala Thr Pro Val Leu Asn Tyr Asp Leu Leu Tyr
        185                 190                 195

Ala Val Ala Lys Leu Gly Pro Gly Glu Lys Tyr Glu Leu His Ala
        200                 205                 210

Gly Thr Glu Ser Thr Pro Ser Val Val His Val Cys Asp Ser
        215                 220                 225

Asp Ile Glu Glu Glu Asp Pro Lys Thr Ser Pro Lys Pro Lys
        230                 235                 240

Ile Ile Gln Thr Arg Arg Pro Gly Leu Pro Pro Ser Val Ser Asn
        245                 250                 255
```

<210> SEQ ID NO 3
<211> LENGTH: 1021
<212> TYPE: DNA
<213> ORGANISM: Rattus norvegicus -continued

```
<220> FEATURE:
<221> NAME/KEY: misc_feature
<223> OTHER INFORMATION: Incyte ID No: 219435_Rn.1

<400> SEQUENCE: 3
aggctgtact gattgtttaa taagaaaata ctacccttttg tctagaactt tctaaataat      60
ggactctggt taatgggtat gagttgactg ggagacatat cacctttttcc tagcccttt     120
gtccgagagg cttaagttac aaggaaggat tctcaaacaa ccaaatacccc aggtgacttc    180
aaggcaatta attttttggac gaacaaggga gaaaaagcat gataagagga gatgcatgtt    240
atcatggacg tgctcagttg gacacggagg gtggcaggcc aggacgccgg gtctggatga    300
ttttttggctt tggggaagtc tttggatcct cctcctcctc caagtcgctg tcacacacgt    360
gcacgacaac gctcggtgta gactcagttc ccgcatgcag ctcatatttc tctcctggtc    420
ctagtttggc cacggcataa aggaggtcgt acgttgagga ctggtgtggc atcgctgata    480
ggcttccagc caacgggagg agatgaaggg ggtgagatga ggaactgttt ggcaggctgt    540
gggggtgcca aactgcagtt tgtctaccat ctgtctctgg ggtctggacc tgtgcaaagt    600
agagtttcag cttcttccct catgaactgg gtccacatga agctcctatc cgggcaccgg    660
gctgcagctt tggggtggct gaaatttatt ccgaacccgt cggaaactct taaacagctg    720
aaacgtcaca cattcgtcat aggtccggaa cagtccctca aattttttcct taacctcctg    780
attggtaaag acctccacat ccaccacaca ggcgaccaga gtggaaacat cacagtccat    840
gctagggggct ggcattcccc tcttcggaat tctcagcgaa gagttaggca gcctcagagt    900
tgggagtgaa gagactcctc tggatggata ctgtcctggt actgccctgc ttctgggggg    960
gaggtggggt gcggtgcggt gctggttgga gactcagcca cctggagcct gctgccgctg   1020
c                                                                   1021

<210> SEQ ID NO 4
<211> LENGTH: 193
<212> TYPE: DNA
<213> ORGANISM: Rattus norvegicus
<220> FEATURE:
<221> NAME/KEY: misc_feature
<223> OTHER INFORMATION: Incyte ID No: 271176_Rn.1

<400> SEQUENCE: 4
tcctggccac ttatatagga ccataagtac acttggcttt gactgcatga gatcccccta      60
tctggtctca cccagtcctc tgcatcccga cattcccagg acatgcacaa tcaccagcat    120
ttattttgat gatttgaggg tatgccccac cttgtggtat cccagccctg tcctgtatag    180
acaagggca tcc                                                        193

<210> SEQ ID NO 5
<211> LENGTH: 1348
<212> TYPE: DNA
<213> ORGANISM: Rattus norvegicus
<220> FEATURE:
<221> NAME/KEY: misc_feature
<223> OTHER INFORMATION: Incyte ID No: 291862_Rn.1

<400> SEQUENCE: 5
ggctacagca atgtctcatg ccaatagata aacgactagc taatttcttt gctgtcaaga      60
tcacctgttt gcaaacaaag atccaagtat cagttgtaag caacttgggt ggcgcttaat    120
ccaagatcgt atacagctga gcatttccga acacaaagga tgatgggtaa acggacggcc    180
cctcccattc atccagtgcc cgtgtgctca aaagttcctt gttttcgtta cctgtgattt    240
```

| | | | | | |
|---|---|---|---|---|---|
| tgtatttctc | tagcccaaag | tgcattacag | aagatacacc | tgcagaacca | tactttctgc | 300 |
| tccatgtgtc | aagcctcatc | tattcctgtt | cattaactag | taactttgga | tgcaaatact | 360 |
| atttaccaca | caacgggcaa | ggacttcaat | gacctaagcc | tccgaattaa | ccaaacaaag | 420 |
| aacactaaca | cagccacctg | atgggggat | tatgtggttt | tttgactaag | gtgtatgtta | 480 |
| gtttcagcag | aaacttcaaa | cctagactga | tcactcagaa | aattaaagtc | cgttctactg | 540 |
| tgaaatatag | caatatagtg | gccggacacg | gtacacgtac | gcgttgagac | cgaggccagc | 600 |
| attgcttgtg | gaatcctgag | tttccacggg | gataacaagt | ctccttttca | aactcagatc | 660 |
| tgaggagtgt | acagcaaagg | ctttgacttt | ccttttgtgg | tggaaggatt | tggttttttc | 720 |
| attggccacg | gaacgactac | aaatagtggc | gagatgctgc | cctctggtgg | ccgaaacgtt | 780 |
| gaactcggtt | gtataggtgg | attgattaca | acagtcaact | cccagggtct | gactttctaa | 840 |
| tccgcgttaa | ctttcaggat | gcaggttctg | agaaagagag | aaaaatgaac | agtctaaatg | 900 |
| agattaaagc | cttggaaata | atttgtgctt | ccaaacaatg | atagcagaga | tttccagttt | 960 |
| agtaaaagtt | gatgtgacta | ccctctgggt | aggcattaag | aactcagtgt | tacagatggc | 1020 |
| ccaggtgatt | agtcttagta | aactgtattg | ccatatgtcg | atgttaacct | gctgcagagc | 1080 |
| aagggattct | cgcactaggt | tgagcacgga | gaggggagaa | ggggagcttt | ccccagaaag | 1140 |
| aatagggaag | ccatgggacc | tcccagcacc | gagaaagtcg | cctctacact | tccttccatg | 1200 |
| atgctcatta | ctgcaaacct | cttgtagcgc | tcgttttaa | gtctgcaaac | gttttaaatg | 1260 |
| gaggggaagg | ggaaggtttc | caccaactga | atcatttgtg | cacgtgtaca | gctcaaagag | 1320 |
| cttagagttc | aaatatatct | ggtgaatg | | | | 1348 |

<210> SEQ ID NO 6
<211> LENGTH: 531
<212> TYPE: DNA
<213> ORGANISM: Rattus norvegicus
<220> FEATURE:
<221> NAME/KEY: misc_feature
<223> OTHER INFORMATION: Incyte ID No: 299263_Rn.1

<400> SEQUENCE: 6

| | | | | | |
|---|---|---|---|---|---|
| gttgactggt | gagacatatc | actcttatcc | tagccctttt | gtccgagagg | cttaatttac | 60 |
| tatggaatgg | attctcaaac | aatccaaaca | cccaggtact | tcaatggtca | attaattttt | 120 |
| ggacgaacaa | gggagaaaaa | gcatgataag | aggagatgca | tgttatacat | ggacgtgctc | 180 |
| agttggacac | ggagaggtgg | caggccagga | cgccgggtta | ctggatagat | ttataaggct | 240 |
| ttggggaagt | cttatggatc | ctacctacct | cctccaagtc | gctgtcacac | acgtagcacg | 300 |
| acaacgctcg | gtagtagact | acagtatccc | gcataacagc | tcatatatta | cactcctggt | 360 |
| cctagtttgg | ccacggcata | aaggaggtcg | tagttgagga | ctggtagtgg | catcgctgat | 420 |
| aggcttccag | ccaacgggag | gagatagaag | ggggtgagat | gaggaactgt | atggcacgct | 480 |
| gtggagggtg | ccaagatgca | gtttagtctc | catctgacta | cagggctg | | 531 |

<210> SEQ ID NO 7
<211> LENGTH: 233
<212> TYPE: DNA
<213> ORGANISM: Rattus norvegicus
<220> FEATURE:
<221> NAME/KEY: misc_feature
<223> OTHER INFORMATION: Incyte ID No: 219652_Rn.1

<400> SEQUENCE: 7

-continued

| aattcctgga ggtaaaattg agcgtggccc caaagagatt cctcagtaga ttctaaacat | 60 |
| cactatcaca taggactacc cagtgctact ggggaggctt gcccgagtga cagagaccga | 120 |
| tttcagacaa acctatttat tataaaagtc tcacagtgtc tgaatgattg tcgtcccccc | 180 |
| ccaccccttt gtatatttgt acagatgttt gagctgtgct tttaaaatct gga | 233 |

<210> SEQ ID NO 8
<211> LENGTH: 615
<212> TYPE: DNA
<213> ORGANISM: Rattus norvegicus
<220> FEATURE:
<221> NAME/KEY: misc_feature
<223> OTHER INFORMATION: Incyte ID No: 206751_Rn.1

<400> SEQUENCE: 8

| gaagatgcta cgagacagcc tgaaatcttg tgaatgacag ccagtcagac ctctgtagca | 60 |
| gcgaccagga agatggaaga ggagatggtc ttcggtgaaa atgaagacga tttggaagag | 120 |
| atgatggacc tcagcgacct gcccacctcc ctctttgctt gcagtgtcca tgaagcggtg | 180 |
| tttgaggtcc aagagcagaa ggagaggttc gaagccctgt tcaccctcta tgatgaccag | 240 |
| gtcacattcc agctgttcaa gagctttcgc agagtgagga tcaacttcag caagcctgag | 300 |
| gctgcggcga gagcacggat cgagctccac gagagtgaat ccatggccg gaagctgaag | 360 |
| ctttacttcg cacaggtgca ggtgtccggg gaggctcggg acaagtccta cttactgcca | 420 |
| ccacagccca ccaagcagtt cctcatctcc cctcccgcct cacccccgt ggggtggaag | 480 |
| cagagtgaag atgccacgcc agtgatcaac tatgacctcc tctgtgccgt ctccaagctg | 540 |
| gggccagggg agaaatacga actgcacgca ggaaccgagt ccaccccag tgtgctggtg | 600 |
| cacgtctgtg agagc | 615 |

<210> SEQ ID NO 9
<211> LENGTH: 297
<212> TYPE: DNA
<213> ORGANISM: Macaca fascicularis
<220> FEATURE:
<221> NAME/KEY: misc_feature
<223> OTHER INFORMATION: Incyte ID No: 702110167H1

<400> SEQUENCE: 9

| cagcagcccc cgggtcgtgc tgggggaccg cggcggggct ctggccgcgg acgggtctg | 60 |
| ggtgcagggc gggggcggcg gcggggtgg ggtttgtctc cagatctgtg gtcagtccgg | 120 |
| gctgcggccg tggggacgga gatctcccgc gacccccctc taggggggcgc gggtcccaag | 180 |
| gagccccttc cccactgctc gtggcccggg ggttcgcctt cctggaagca gcagcaggaa | 240 |
| tgagggggaga atcatacttc atcggaatga ggagcccggg acagcagtga cacatcc | 297 |

<210> SEQ ID NO 10
<211> LENGTH: 192
<212> TYPE: PRT
<213> ORGANISM: Homo sapiens
<220> FEATURE:
<221> NAME/KEY: misc_feature
<223> OTHER INFORMATION: Incyte ID No: g1435040

<400> SEQUENCE: 10

Met Asp Cys Asp Val Ser Thr Leu Val Ala Cys Val Val Asp Val
 1               5                  10                  15

Glu Val Phe Thr Asn Gln Glu Val Lys Glu Lys Phe Gly Gly Leu
                20                  25                  30

```
Phe Arg Thr Tyr Asp Asp Cys Val Thr Phe Gln Leu Phe Lys Ser
                 35                  40                  45

Phe Arg Arg Val Arg Ile Asn Phe Ser Asn Pro Lys Ser Ala Ala
             50                  55                  60

Arg Ala Arg Ile Glu Leu His Glu Thr Gln Phe Arg Gly Lys Lys
         65                  70                  75

Leu Lys Leu Tyr Phe Ala Gln Val Gln Thr Pro Glu Thr Asp Gly
             80                  85                  90

Asp Lys Leu His Leu Ala Pro Pro Gln Pro Ala Lys Gln Phe Leu
             95                 100                 105

Ile Ser Pro Ser Ser Pro Val Ser Trp Gln Pro Ile Asn
        110                 115                 120

Asp Ala Thr Pro Val Leu Asn Tyr Asp Leu Leu Tyr Ala Val Ala
            125                 130                 135

Lys Leu Gly Pro Gly Glu Lys Tyr Glu Leu His Ala Gly Thr Glu
            140                 145                 150

Ser Thr Pro Ser Val Val His Val Cys Asp Ser Asp Ile Glu
            155                 160                 165

Glu Glu Glu Asp Pro Lys Thr Ser Pro Lys Pro Lys Ile Ile Gln
            170                 175                 180

Thr Arg Arg Pro Gly Leu Pro Pro Ser Val Ser Asn
            185                 190
```

<210> SEQ ID NO 11
<211> LENGTH: 241
<212> TYPE: PRT
<213> ORGANISM: Homo sapiens
<220> FEATURE:
<221> NAME/KEY: misc_feature
<223> OTHER INFORMATION: Incyte ID No: g6017919

<400> SEQUENCE: 11

```
Met Leu Arg Asp Thr Met Lys Ser Trp Asn Asp Ser Gln Ser Asp
  1               5                  10                  15

Leu Cys Ser Thr Asp Gln Glu Glu Glu Glu Met Ile Phe Gly
             20                  25                  30

Glu Asn Glu Asp Asp Leu Asp Glu Met Met Asp Leu Ser Asp Leu
             35                  40                  45

Pro Thr Ser Leu Phe Ala Cys Ser Val His Glu Ala Val Phe Glu
             50                  55                  60

Ala Arg Glu Gln Lys Glu Arg Phe Glu Ala Leu Phe Thr Ile Tyr
             65                  70                  75

Asp Asp Gln Val Thr Phe Gln Leu Phe Lys Ser Phe Arg Arg Val
             80                  85                  90

Arg Ile Asn Phe Ser Lys Pro Glu Ala Ala Arg Ala Arg Ile
             95                 100                 105

Glu Leu His Glu Thr Asp Phe Asn Gly Gln Lys Leu Lys Leu Tyr
            110                 115                 120

Phe Ala Gln Val Gln Met Ser Gly Glu Val Arg Asp Lys Ser Tyr
            125                 130                 135

Leu Leu Pro Pro Gln Pro Val Lys Gln Phe Leu Ile Ser Pro Pro
            140                 145                 150

Ala Ser Pro Pro Val Gly Trp Lys Gln Ser Glu Asp Ala Met Pro
            155                 160                 165

Val Ile Asn Tyr Asp Leu Leu Cys Ala Val Ser Lys Leu Gly Pro
            170                 175                 180
```

```
Gly Glu Lys Tyr Glu Leu His Ala Gly Thr Glu Ser Thr Pro Ser
            185                 190                 195

Val Val Val His Val Cys Glu Ser Glu Thr Glu Glu Glu Glu
            200                 205                 210

Thr Lys Asn Pro Lys Gln Lys Ile Ala Gln Thr Arg Arg Pro Asp
            215                 220                 225

Pro Pro Thr Ala Ala Leu Asn Glu Pro Gln Thr Phe Asp Cys Ala
            230                 235                 240

Leu

<210> SEQ ID NO 12
<211> LENGTH: 3184
<212> TYPE: DNA
<213> ORGANISM: Homo sapiens
<220> FEATURE:
<221> NAME/KEY: misc_feature
<223> OTHER INFORMATION: Incyte ID No: g1435039

<400> SEQUENCE: 12
ctctgctgtg ctgcctcaaa cgcggagggc tgcgtgcagt gggagcgggc tccaggagcc      60
cgagcctcca gccgtcctca gagcaaggca gcaccgaggc ctggccacag caatatccat     120
ctggaagctc ttcccttcac tcccaactct gaggttgcct aactctttat taaaaattca     180
gaaggggaa tgccagcccc tagcatggac tgtgatgttt ccactctggt tgcctgtgtg      240
gtggatgtcg aggtctttac caatcaggag gttaaggaaa aatttggggg actgtttcgg     300
acttatgatg actgtgtgac gttccagcta tttaagagtt tcagacgtgt ccgtataaac     360
ttcagcaatc ctaaatctgc agcccgagct aggatagagc ttcatgaaac ccaattcaga     420
gggaaaaaat taaagctcta ctttgcacag gttcagactc cagagacaga tggagacaaa     480
ctgcacttgg ctccacccca gcctgccaaa cagtttctca tctcgccccc ttcctcccca     540
cctgttagct ggcagcccat caacgatgcc acgccagtcc tcaactatga cctcctctat     600
gctgtggcca aactaggacc aggagagaag tatgagctcc atgcagggac tgagtccacc     660
ccaagtgtcg tcgtgcacgt gtgcgacagt gacatagagg aagaagagga cccaaagact     720
tccccaaagc caaaaatcat ccaaactcgg cgtcctggcc tgccaccctc cgtgtccaac     780
tgagctgcct gctccttctc gataatagcc gtctcctctt tatcatgctt tttccccctg     840
ttgtttgtca aaaaaaattg cctttaaatt cctgggtgtt tggttgtttg agattccttc     900
cttgttatca agcctctcgg acaaagggc taggaaaagg tgatatgtct cctgatcata     960
tcatacccat taagtataac ccattattta gaaggttcta gggaaaaaag tagtattttc    1020
ttattaaaca atcagcacag cctatatctt tgttctctca tgttgatcca agccagagac    1080
atcggtaaca aatagcacct gtgttgtttg tgaggtgttt cagtcccagt cctgatgtgt    1140
gtgcgttgtt ctctcctggc cacttaaata ggaccatatg taaacttgac tttgactgca    1200
tgagatatcc ctatctggtc tcactcagtc tctgcatcc caacattccc aggacatgca     1260
tgatcaccag catttatttt cattatttga ggatatctta taactcacag attgtcagca    1320
tccagccatg tcctatctag attaggaaaa tgatcagaat attccagctc aacaagtctg    1380
ggtatactca ctattgtgag tcaatacacc atagctctgt tgaaattcct ggaggcaaaa    1440
ttgaccttgg ccccaaagat attcctcaat agatttcaaa caccactccc ctgtagaact    1500
ctcccagcct cgttggggag gcttgtccag ggtgatagag actgatttca gacaaaccta    1560
tttattacaa aagtttcatg gtgtctgaat gattgttttc tctctttgta tatttgtaca    1620
```

-continued

| | |
|---|---|
| aatgtttcag ctgtgctttt aaaaaatctg atgttttttt atttagtgat tgttcgacaa | 1680 |
| ttagctgctt caaaacataa tgtgcattgc ttatgaatgc cttcatatac taatacagat | 1740 |
| actctgataa tattcactc taataaggat aatgctgaat tttgaaagga cacaaaacat | 1800 |
| ctaatgccaa tatatacatg gttagccaac atctttgcta tcaagaccac ttgtttaaa | 1860 |
| taaagatgca agtgtcagtt gtagattatt gggatgaagc taaatcccca gaatgcagca | 1920 |
| gcagctgagc atgttaaaat ggggaaggat gatagctaca tgtatgccgg tcctactcac | 1980 |
| gcgacacccg tgtgctcaaa aaagttactt gttttgtta cgtgtgattt tcctatttct | 2040 |
| ctagcccaaa gtgcattaca aagatacac ctatagaacc attaccttct gctatgtgtg | 2100 |
| ccagggctca tctactcctg tacattaatg gattacttta gatgcaaatg cagattacaa | 2160 |
| tggagtgggg aagtactttc attacccaag cctcagaaaa acacacaaga acaataacac | 2220 |
| agcaaacaga ttgagggatt gttgtggttt ttgactaagg tgtatgttag tttcatcaga | 2280 |
| aacttaaaac atagactgat cactcagaaa ttaaagtccg tttactgtg aatatagcaa | 2340 |
| tatagtactg gacacagtac tggtgaaact gaggagagca ttgcttgtaa atcctgagt | 2400 |
| ttccataagg aaaatgaaaa ctccttttaa aaataaaatc tgaggagtgt acaataagca | 2460 |
| tatgctttga ctttcctttg ctgtggaggt ttttggtttt tcattgatga taaacgacta | 2520 |
| cagacttagt agtggagaaa tggtgtcctc tagtggaaga aatagtagct ccgctattca | 2580 |
| gatgcagagc actgcagcat ccagcctttc aaagctgact cttctcaatc atctgtgggt | 2640 |
| catttgactt gattttttaa gctaccctga atttccagaa tgcaggttct aaagaaatct | 2700 |
| agatgagaga aagtatttga aaatgatttt taaatgtttt ttaaaagaca catctgacat | 2760 |
| tttttaacaac ttagtaaaag ttgaaatgac cattctgtgt agtcataaaa gaaacacaat | 2820 |
| gaagtgtatg gcctctggag ttagtcttag taaaacttat tgctctgtgt caatgttaac | 2880 |
| ctgtctcaga tcaagtaatt ccttcactag gttgggtttg gggaggggg aaaagagggg | 2940 |
| cttttcctag gagaacgata agaaatgaa agactccttg aagtgttgca agggaacctc | 3000 |
| ctagcactgt gaaagtcaga atcgcctcag catttccatg acgcacatta tgcaaatctc | 3060 |
| tttagcacta ttttaaggtt gaaaacttta acaatgaagg ggaagggaa gatttccacc | 3120 |
| aactgaatca tttgtgcacg tgtatagctc aaagagctta gacttcaaat atatctggtg | 3180 |
| aatg | 3184 |

<210> SEQ ID NO 13
<211> LENGTH: 828
<212> TYPE: DNA
<213> ORGANISM: Homo sapiens
<220> FEATURE:
<221> NAME/KEY: misc_feature
<223> OTHER INFORMATION: Incyte ID No: g6017918

<400> SEQUENCE: 13

| | |
|---|---|
| aaaaggccca ctttgggga taatgctgag ggacactatg aaatcttgga atgatagcca | 60 |
| gtcagatctg tgtagcactg accaagaaga ggaagaagag atgattttg gtgaaaatga | 120 |
| agatgatttg gatgagatga tggatttaag tgatctgcct acctcacttt ttgcttgcag | 180 |
| cgtccatgaa gcagtgtttg aggcacgaga gcagaaggaa agatttgaag cactcttcac | 240 |
| catctatgat gaccaggtta ctttcagct gttaaaagc tttagaagag tcagaataaa | 300 |
| tttcagcaaa cctgaagcgg cagcaagagc gcgaatagaa ctccacgaaa cagacttcaa | 360 |
| tgggcagaag ctaaagctat attttgcaca ggtgcagatg tccggcgaag tgcgggacaa | 420 |

```
gtcctatctc ctgccgcccc agcctgtcaa gcagttcctc atctcccctc cagcctctcc    480
cccagtgggg tggaagcaga gcgaagatgc gatgcctgtt ataaattatg atttactctg    540
tgctgtttcc aaattgggac caggagagaa atatgaactt cacgcgggaa cagagtcgac    600
acccagcgtg gtggttcatg tctgtgaaag tgaaactgaa gaggaagaag agacaaaaaa    660
ccccaaacag aaaattgccc agacaaggcg ccccgaccct ccgaccgcag cgttgaatga    720
gccccagacc tttgattgcg cgctgtgagg cccttggttg tggtgcgagg cggctgccct    780
ggtgggctct ggccatggcg ctctgtgcct gcggccgatg cgttgctg                 828
```